(12) United States Patent
Horstmann et al.

(10) Patent No.: US 9,114,240 B2
(45) Date of Patent: Aug. 25, 2015

(54) TRANSDERMAL THERAPEUTIC SYSTEM REINFORCED BY ULTRASOUNDS

(75) Inventors: Michael Horstmann, Neuwied (DE); Andreas Koch, Melsbach (DE)

(73) Assignee: Michael Horstmann, Neuwied (DE)

( * ) Notice: Subject to any disclaimer, the term of this patent is extended or adjusted under 35 U.S.C. 154(b) by 936 days.

(21) Appl. No.: 12/303,470

(22) PCT Filed: May 11, 2007

(86) PCT No.: PCT/EP2007/004173
§ 371 (c)(1),
(2), (4) Date: Dec. 4, 2008

(87) PCT Pub. No.: WO2007/147461
PCT Pub. Date: Dec. 27, 2007

(65) Prior Publication Data
US 2009/0192431 A1      Jul. 30, 2009

(30) Foreign Application Priority Data

Jun. 24, 2006   (DE) .................... 10 2006 028 987

(51) Int. Cl.
*A61M 37/00* (2006.01)
*A61N 7/00* (2006.01)
*A61K 9/00* (2006.01)

(52) U.S. Cl.
CPC ... *A61M 37/0092* (2013.01); *A61M 2037/0007* (2013.01); *A61N 7/00* (2013.01)

(58) Field of Classification Search
None
See application file for complete search history.

(56) References Cited

U.S. PATENT DOCUMENTS

| 4,787,888 | A | | 11/1988 | Fox |
| 5,415,629 | A | * | 5/1995 | Henley ........................ 604/20 |
| 5,714,162 | A | * | 2/1998 | Muller ....................... 424/448 |
| 6,121,508 | A | * | 9/2000 | Bischof et al. ............... 602/52 |
| 6,884,434 | B1 | | 4/2005 | Muller et al. |
| 2005/0112135 | A1 | * | 5/2005 | Cormier et al. ............ 424/185.1 |
| 2007/0081977 | A1 | * | 4/2007 | Horstmann ................. 424/93.2 |

FOREIGN PATENT DOCUMENTS

| DE | 198 14 084 A1 | 10/1999 |
| WO | WO 02/056939 A2 | 7/2002 |
| WO | WO 2005049128 A1 * | 6/2005 ........... A61M 37/00 |
| WO | WO 2005/069758 A2 | 8/2005 |

* cited by examiner

*Primary Examiner* — Michael B Pallay
(74) *Attorney, Agent, or Firm* — Panitch Schwarze Belisario & Nadel LLP

(57) ABSTRACT

The invention relates to a transdermal therapeutic system (10) comprising a pharmaceutical active agent formulation (13), an adhesive layer (11) comprising a contact surface (12), and at least one ultrasound transmitter (21), the side of the ultrasound transmitter opposing the contact surface being directly or indirectly adjacent to the pharmaceutical active agent formulation. The transdermal therapeutic system is a multi-layered laminate, one of the laminate layers comprising the ultrasound transmitter, another comprising the adhesive layer, and another comprising the pharmaceutical active agent formulation. Furthermore, from a top view, at least in a plane position of the transdermal therapeutic system, all of the laminate layers (11, 21, 14) are at least approximately mutually congruent and are at least approximately the size of the contact surface. The inventive system provides an ultrasound-reinforced transdermal therapeutic system characterized by an extensive use of active agents, enabling an improved absorption of active agents through the skin.

28 Claims, 2 Drawing Sheets

TRANSDERMAL THERAPEUTIC SYSTEM REINFORCED BY ULTRASOUNDS

The invention relates to a transdermal therapeutic system with a pharmaceutical active substance formulation, with an adhesive layer comprising a contact surface, and with at least one ultrasound transmitter, which ultrasound transmitter, at least on the side directed away from the contact surface, is directly or indirectly adjacent to the pharmaceutical active substance formulation.

A device of this kind is known from U.S. Pat. No. 4,787,888. The active substance is dissolved in a highly viscous solution and stored in an active substance reservoir surrounded by a securing flange that contains adhesive. The highly viscous solution damps the oscillations from the ultrasound transmitter. The delivery of the active substance is restricted to a small surface area of the skin. This permits only a slow diffusion of the active substance into the skin and a low degree of utilization of active substance. Combination with other measures that promote resorption is not possible.

Thus, the object of the present invention is to develop an ultrasound-reinforced transdermal therapeutic system which permits a high degree of utilization of active substance and improved uptake of active substance through the skin.

This object is achieved by the features of the main claim. To this end, the transdermal therapeutic system is a multi-layered laminate, one laminate layer comprising the ultrasound transmitter, one laminate layer comprising the adhesive layer, and one laminate layer comprising the pharmaceutical active substance formulation. Furthermore, in a top view, at least with the transdermal therapeutic system lying flat, all of the laminate layers are at least approximately congruent to one another and are at least approximately the size of the contact surface.

Further details of the invention are set forth in the dependent claims and in the following description of schematically illustrated embodiments.

Figure 1:
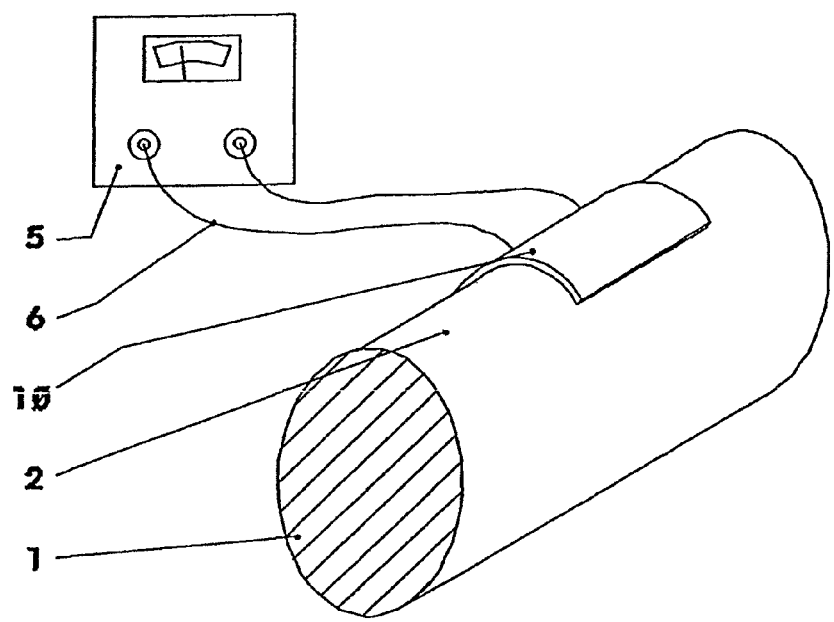
Figure 2:
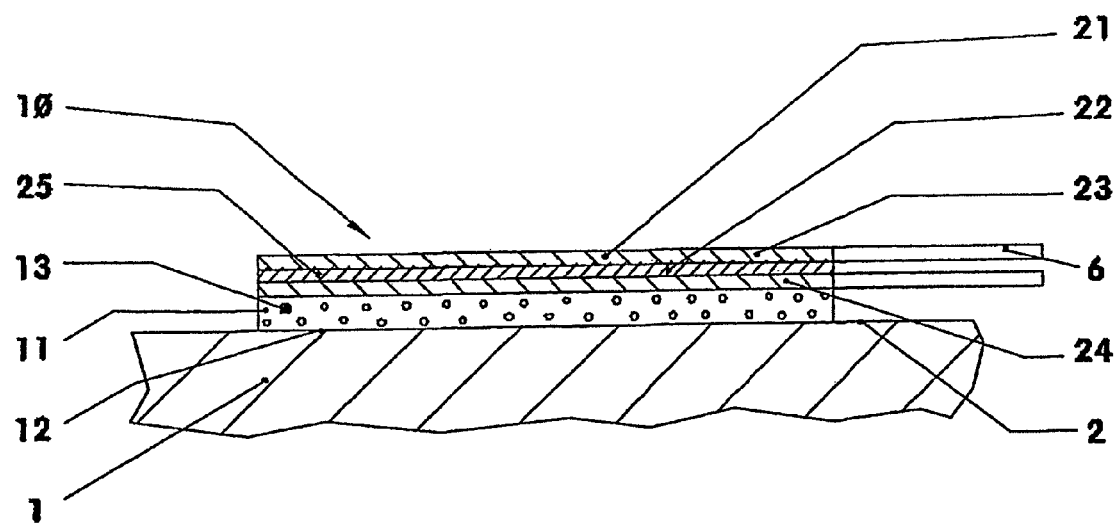
Figure 3:
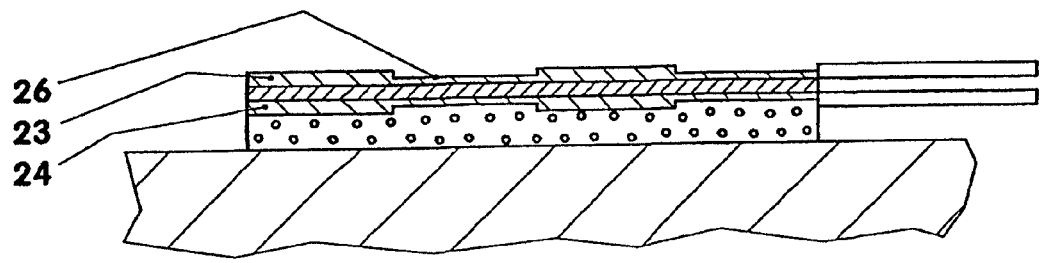
Figure 4:
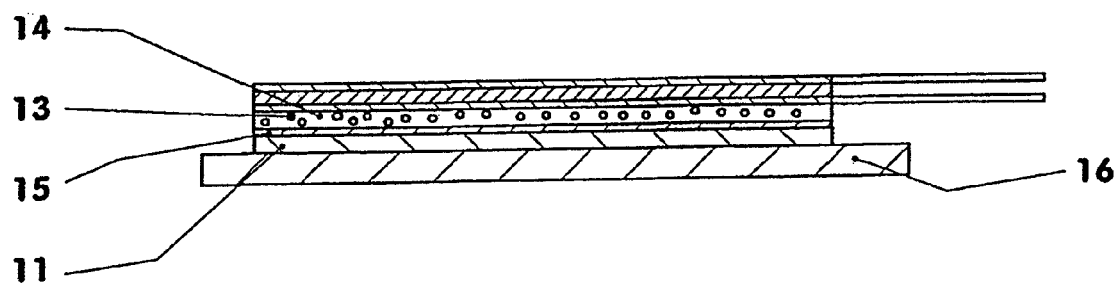
Figure 5:
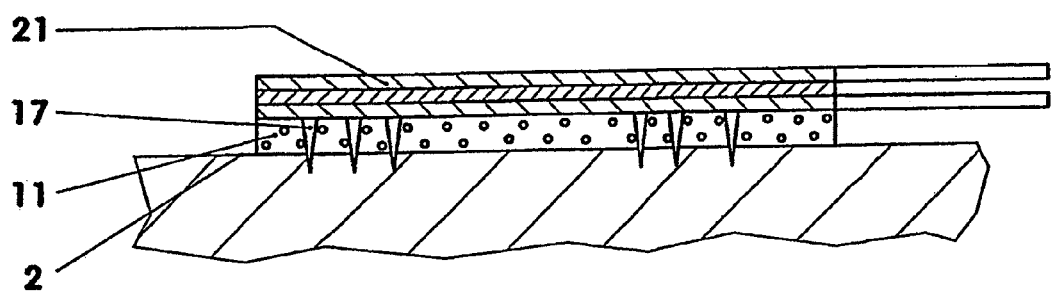

FIG. 1: Transdermal therapeutic system in use;
FIG. 2: Partial longitudinal section through FIG. 1;
FIG. 3: Therapeutic system with segmentations;
FIG. 4: Therapeutic system with a membrane;
FIG. 5: Therapeutic system with microneedles.

FIG. 1 shows a transdermal therapeutic system (10) during use, e.g. on an arm (1) of a patient. The transdermal therapeutic system (10) is an active-substance-containing medical product (10) affixed to the arm (1) and comprising an integrated ultrasound transmitter (21). The ultrasound transmitter (21) is here connected by leads (6) to an oscillator (5), which is connected electrically to a power source.

FIG. 2 shows a partial longitudinal section of FIG. 1. The transdermal therapeutic system (10) is structured as a multi-layered laminate. It here comprises, as the bottom laminate layer, an adhesive laminate layer (11) which adheres to the patient's skin (2) via a contact surface (12) and in which a pharmaceutical active substance formulation (13) is incorporated. The ultrasound transmitter (21), as a further laminate layer (21); is connected to this first laminate layer (11) across the entire surface area. Therefore, at least in a top view of the transdermal therapeutic system (10) when lying flat, the ultrasound transmitter (21) is at least approximately congruent to the adhesive layer (11). Both layers (11, 21) are the size of the contact surface (12) in this illustrative embodiment. If appropriate, an inert separating film lies between the adhesive layer (11) and the ultrasound transmitter (21) and prevents chemical reactions between the adhesive layer (11) and the ultrasound transmitter (21).

In this illustrative embodiment, the transdermal therapeutic system (10) has a square base surface with an edge length of 80 millimeters. However, the base surface can also be rectangular, round, etc. The thickness of the system (10) is in this case between 500 and 600 micrometers', for example.

The adhesive layer (11), with the incorporated pharmaceutical active substance formulation (13), is a lipophilic, semi-solid composition, for example, in which the individual constituents may be present in separate matrices or in a monolithic reservoir matrix and adhesive matrix. For example, the pharmaceutical active substance formulation (13) can be dissolved or dispersed in a monolithic reservoir matrix and adhesive matrix.

Here, the adhesive layer (11) is 200 micrometers thick, but it can also be made thinner. The matrix of the adhesive layer can comprise copolymers with acrylic acid ester, mixtures of rubbers, polybutylene, polyisobutylene and resins, polyvinyl acetate, silicone polymers, etc. These materials are safe for use on the skin (2) of the patient. The matrix can contain up to 40% fillers, e.g. titanium oxide, zinc oxide, chalk, activated charcoal, finely dispersed silica, etc. The adhesive layer (11) is pressure-sensitive, for example. This means that the adhesive action of the layer (11) on the skin (2) is strengthened by external pressure.

The ultrasound transmitter (21) is, for example, a thickness transducer with a piezoelectric element (22).

The piezoelectric element (22) comprises, for example, a piezoelectric film (25) and two electrodes (23, 24). The piezoelectric film (25) consists, for example, of a dielectric material or a material that has acquired its piezoelectric properties through mechanical or electrical treatment. For example, a spontaneous, remanent polarization can be achieved by applying a direct voltage at a temperature below the Curie temperature. The film used in this illustrative embodiment is a polymer film, e.g. of polyvinylidene fluoride (PVDF), polyvinylidene chloride (PVDC), etc. It has a thickness of between 5 micrometers and 25 micrometers, for example.

The electrodes (23, 24) are arranged on both sides of the film (25). For example, in order to generate the electrodes (23, 24), the film (25) is coated on both sides with an electrically conductive metal layer in a metal vapor deposition process. The material of the electrodes (23, 24) is a skin-compatible material. This can be, for example, aluminum, silver, copper, zinc, gold, a polymer formulation made conductive by carbon, etc. The thickness of the piezoelectric element (22) is here between 10 micrometers and 100 micrometers, although the thickness can be up to 300 micrometers.

Instead of the thickness transducer described here, the ultrasound transmitter can comprise a composite transducer which, for example, has additional compounds for setting its resonance frequency.

To produce the transdermal therapeutic system (10), the adhesive layer (11) with the incorporated active substance formulation (13) is produced by means of coating, vaporization and drying processes. By virtue of the small thickness of the layer, the gel-like composition thus produced, for example, has a substantially homogeneous composition. For example, the adhesive layer (11) is applied to a protective film (16), cf. FIG. 4. The protective film (16) is not removed from the transdermal therapeutic system (10) until immediately before the latter is put to use.

The ultrasound transmitter (21) is laminated onto the adhesive layer (11), for example with a separating film being located between them. The ultrasound transmitter (21) then lies across the full surface area of the adhesive layer (11) or the separating film.

After lamination onto the adhesive layer (11), the ultrasound transmitter (21) adjoins the active substance formulation (13) at least indirectly. For example, at a high active substance concentration, the bottom electrode (24) of the ultrasound transmitter (21) can directly contact the active substance formulation (13).

To use the transdermal therapeutic system (10), it is affixed to the skin (2), e.g. of the arm (1), after the protective film (16) has been peeled off.

The active substance formulation (13) passes through the adhesive layer (11) and the skin (2) into the arm (1). The diffusion rate is initially low, since the epidermis, the outer layer of the skin (2), allows only a small flow of active substance to pass thorough.

The ultrasound transmitter (21) is attached electrically to the oscillator (5) and the power source is then switched on. The voltage applied to the ultrasound transmitter (21) here is between 10 volts and 40 volts, for example. The ultrasound transmitter (21) can be operated using voltage of between 2 volts and 1000 volts. The frequency of the alternating current applied is between 20 kHz and 100 kHz in this illustrative embodiment.

The piezoelectric film (25) is deformed on account of the electrical voltage applied between the electrodes (23, 24). By means of this inverse piezoelectric effect, the alternating voltage generated by the oscillator (5) excites the film (25) to oscillate in a direction normal to the arm (1).

The oscillating piezoelectric element (22) transmits some of the oscillation energy to the active-substance-containing adhesive layer (11) and into the skin (2). In the adhesive layer (11), the energy delivered causes an increase in the kinetic energy of the pharmaceutical active substance formulation (13). The oscillations transmitted into the skin (2) experience only slight damping during their travel, e.g. by virtue of the gel-like, thin adhesive layer (11). The epidermis is activated by the delivery of ultrasound energy and is made permeable to active substance. The barrier effect of the epidermis is effectively breached. The diffusion of the active substance formulation (13) through the adhesive layer (11) and the skin (2) is intensified. The diffusion into the skin (2) is here effected across the entire contact surface (12) of the transdermal therapeutic system (10) with the skin (2). Moreover, the large contact surface (12) allows the active substances to be passed through the skin (2) in a manner substantially free of pain. The small layer thickness of the active-substance-containing adhesive layer (11) means that the diffusion paths are short. In this way, a high degree of utilization of active substance is achieved.

FIG. 3 shows a further transdermal therapeutic system (10). In this system (10), the electrodes (23, 24) have segmentations (26), e.g. interruptions. During use of the transdermal therapeutic system (10), the areas of the segmentations (26) are excited only slightly. Thus, for example, the release of active substance through the skin (2) can be limited in certain areas, while in other areas the release of active substance is intensified by the ultrasound transmitter (21).

FIG. 4 shows a transdermal therapeutic system (10) in which the active substance formulation (13) is incorporated in an active-substance-containing layer (14). This layer (14) has a gel-like consistency, for example. It has a thickness of 300 micrometers, for example, and is here separated from the adhesive layer (11) by a membrane (15) which is permeable at least in some areas to the active substance formulation (13). The thickness of the membrane is between 10 micrometers and 50 micrometers. On the side directed away from the contact surface (12), the ultrasound transmitter (21) adjoins the active-substance-containing layer (14). The ultrasound transmitter (21) is structured, for example, in the manner described with reference to FIG. 2 or FIG. 3. If appropriate, a separating film can be arranged between the ultrasound transmitter (21) and the active-substance-containing laminate layer (14). The transdermal therapeutic system is in this case protected, prior to its use, by means of a protective film (16).

During use of the transdermal therapeutic system (10), the active substance formulation (13) passes through the for example semipermeable membrane (15) and diffuses through the adhesive layer (11) and through the skin (2). As has been described above, the diffusion is intensified by the influence of the ultrasound transmitter (21). In this illustrative embodiment too, the large contact surface (12) allows the system to be used substantially free of pain and permits a high degree of utilization of active substance.

In all the illustrative embodiments described, the piezoelectric element (22) can have separate electrodes (23, 24) that bear on the piezoelectric film (25). The electrode (23) remote from the contact surface can also be made rigid and the other electrode (24) can oscillate. The entire transdermal therapeutic system (10) can be protected by means of a band, e.g. a textile band. This band is then arranged such that it does not prevent the oscillations of the piezoelectric element (22).

The oscillator (5) can be arranged on the transdermal therapeutic system (10). When using such a system (10), the oscillator (5) is connected to a source of direct or alternating current.

It is also possible for the ultrasound transmitter (21) to be designed with capacitive elements.

FIG. 5 shows a transdermal therapeutic system (10) reinforced by ultrasound and having additional resorption capacity. In order to improve the delivery of active substance through the skin (2), the transdermal therapeutic system (10) comprises micro-needles (17), which are arranged in groups for example. These microneedles (17) are secured, for example, on the bottom electrode (24) of the ultrasound transmitter (21) and protrude several tenths of a millimeter from the contact surface (12), at least when the transdermal therapeutic system (10) is in use. The transdermal therapeutic system (10) can here be structured in the manner described with reference to the aforementioned FIGS. 2-4.

When using the transdermal therapeutic system (10) shown in FIG. 5, the microneedles pass through the epidermis. In doing so, they fix the transdermal therapeutic system (10) and stretch the epidermis between the needles (17), as a result of which the epidermis is permeable to active substance within certain areas or at points. The oscillating ultrasound transmitter (21) causes a working stroke of the microneedles (17). In this way, the energy emitted by the ultrasound transmitter (21) is additionally applied in a punctiform manner to the skin (2). This has the effect of ensuring improved diffusion of active substance through the skin (2).

The microneedles (17) have undercuts, for example. These act as barbs during use of the transdermal therapeutic system (10). It is also conceivable for the microneedles (17) to be designed with a screw-shaped structure. These microneedles (17) are then mounted in the axial and radial directions on the bottom electrode (24). They are thus mounted so as to rotate freely. The oscillating electrode (24) of the ultrasound transmitter (21) then causes a rotation of the microneedle (17) in the manner of a drilling movement on penetration into the epidermis. In these transdermal therapeutic systems (10), the microneedles (17) can also be arranged in such a way that they do not protrude from the contact surface (12) until the system (10) is put to use.

It is also conceivable to use chemical permeation enhancers in the adhesive layer (11). These can be volatile additives, for example alcohols, fatty acids, carboxylic acids, esters, etc. They can act on the skin (2) across the whole contact surface (12). The permeation of the active substance through the skin (2) is additionally strengthened by this means.

LIST OF REFERENCE NUMBERS 1 arm
2 skin
5 oscillator
6 leads
10 transdermal therapeutic system, medical product containing active substance
11 adhesive layer, laminate layer
12 contact surface
13 pharmaceutical active substance formulation
14 active-substance-containing layer, laminate layer
15 membrane
16 protective film
17 microneedles
21 ultrasound transmitter, laminate layer
22 piezoelectric element
23 electrodes, remote from (3)
24 electrode, directly or indirectly adjacent to (13)
25 film
26 segmentations

The invention claimed is:

1. A transdermal therapeutic system comprising a multi-layer laminate containing a pharmaceutical active substance formulation incorporated in an adhesive layer, the system including:
the adhesive layer having a first side comprising a skin contact surface for adhering to skin to be treated and a second side facing away from the skin contact surface; and
an ultrasound transmitter layer located on the second side of the adhesive layer and comprising an ultrasound transmitter and microneedles mounted on and extending from the ultrasound transmitter into the adhesive layer and through the skin contact surface of the adhesive layer;
wherein the ultrasound transmitter is directly adjacent to the adhesive layer having the pharmaceutical active substance formulation incorporated therein; and
wherein, at least in a top view with the transdermal therapeutic system lying flat, the layers of the multilayer laminate are at least congruent to one another and have a size at least as great as a size of the skin contact surface.

2. The transdermal therapeutic system according to claim 1, wherein the ultrasound transmitter further comprises two electrodes.

3. The transdermal therapeutic system according to claim 2, wherein said electrodes are arranged on both sides of a piezoelectric polymer film and one of the electrodes is directly adjacent to the layer containing the pharmaceutical active substance formulation, wherein said microneedles are attached to the latter mentioned electrode.

4. The transdermal therapeutic system according to claim 2, wherein the electrodes have segmentations.

5. The transdermal therapeutic system according to claim 2, wherein one of the two electrodes is in direct contact with the active substance-containing adhesive layer.

6. The transdermal therapeutic system according to claim 2, wherein one of the two electrodes is in direct contact with the active substance-containing adhesive layer, and the microneedles are mounted on this electrode.

7. The transdermal therapeutic system according to claim 1, wherein the microneedles protrude from the skin contact surface of the adhesive layer, at least during use of the transdermal therapeutic system.

8. The transdermal therapeutic system according to claim 7, wherein the microneedles have screw-shaped contours and are mounted in axial and radial directions on the ultrasound transmitter.

9. The transdermal therapeutic system according to claim 8, wherein the ultrasound transmitter further comprises two electrodes, and wherein oscillation of an electrode causes rotation of the microneedles, and the ultrasound transmitter comprises a piezo-electric polymer film.

10. The transdermal therapeutic system according to claim 7, wherein the microneedles have barbs.

11. The transdermal therapeutic system according to claim 1, wherein the adhesive layer comprises a lipophilic, pressure-sensitive composition.

12. The transdermal therapeutic system according to claim 1, wherein the adhesive layer comprises chemical permeation enhancers.

13. The transdermal therapeutic system according to claim 1, wherein individual layers of the multi-layer laminate have a thickness of less than 300 micrometers.

14. The transdermal therapeutic system according to claim 1, wherein the multi-layer laminate has a total thickness of less than 600 micrometers.

15. A transdermal therapeutic system comprising a multi-layer laminate containing a pharmaceutical active substance formulation and including:
an adhesive layer having a first side comprising a skin contact surface for adhering to skin to be treated and a second side facing away from the skin contact surface; and
an ultrasound transmitter layer located on the second side of the adhesive layer and comprising an ultrasound transmitter and microneedles mounted on and extending from the ultrasound transmitter into the adhesive layer and through the skin contact surface of the adhesive layer;
a layer containing the pharmaceutical active substance formulation, said layer being interposed between the adhesive layer and the ultrasound transmitter layer;
wherein the ultrasound transmitter is directly adjacent to the layer containing the pharmaceutical active substance formulation; and
wherein, at least in a top view with the transdermal therapeutic system lying flat, the layers of the multilayer laminate are at least congruent to one another and have a size at least as great as a size of the skin contact surface.

16. The transdermal therapeutic system according to claim 15, further comprising a membrane arranged between the adhesive layer and the layer containing the pharmaceutical active substance formulation, wherein the membrane is permeable at least to the pharmaceutical active substance.

17. The transdermal therapeutic system according to claim 15, wherein the ultrasound transmitter further comprises two electrodes.

18. The transdermal therapeutic system according to claim 17, wherein the electrodes have segmentations.

19. The transdermal therapeutic system according to claim 15, wherein the microneedles protrude from the skin contact surface, at least during use of the transdermal therapeutic system.

20. The transdermal therapeutic system according to claim 19, wherein the microneedles have screw-shaped contours and are mounted in axial and radial directions on the ultrasound transmitter.

21. The transdermal therapeutic system according to claim 20, wherein the ultrasound transmitter further comprises two electrodes, and wherein oscillation of an electrode causes rotation of the microneedles, and the ultrasound transmitter comprises a piezo-electric polymer film.

22. The transdermal therapeutic system according to claim 19, wherein the microneedles have barbs.

23. The transdermal therapeutic system according to claim 15, wherein the adhesive layer comprises a lipophilic, pressure-sensitive composition.

24. The transdermal therapeutic system according to claim 15, wherein the adhesive layer comprises chemical permeation enhancers.

25. The transdermal therapeutic system according to claim 15, wherein individual layers of the multi-layer laminate have a thickness of less than 300 micrometers.

26. The transdermal therapeutic system according to claim 15, wherein the multi-layer laminate has a total thickness of less than 600 micrometers.

27. The transdermal therapeutic system according to claim 15, wherein the ultrasound transmitter further comprises two electrodes that are arranged on both sides of a piezoelectric polymer film, wherein one of the electrodes is directly adjacent to the layer containing the pharmaceutical active substance formulation, and wherein said microneedles are attached to the latter mentioned electrode.

28. The transdermal therapeutic system according to claim 15, wherein one of the two electrodes is in direct contact with the layer containing the active substance formulation.

* * * * *